United States Patent [19]
Yuhta et al.

[11] Patent Number: 5,462,362
[45] Date of Patent: Oct. 31, 1995

[54] WEAR RESISTING SLIDE MEMBER

[75] Inventors: Toshio Yuhta; Ikuya Nishimura; Daijiro Kano, all of Hokkaido; Tsuyoshi Saitou, Kanagawa; Tomita Suzuki, Kanagawa; Mamoru Tanaka, Kanagawa, all of Japan

[73] Assignee: NSK Ltd., Tokyo, Japan

[21] Appl. No.: 236,082

[22] Filed: May 2, 1994

[30] Foreign Application Priority Data

Apr. 30, 1993 [JP] Japan ................................. 5-127835

[51] Int. Cl.$^6$ .................................................. F16C 17/00
[52] U.S. Cl. ................................................. 384/13; 384/293
[58] Field of Search ........................... 384/13, 293, 291, 384/292, 284, 285

[56] References Cited

U.S. PATENT DOCUMENTS

| | | | |
|---|---|---|---|
| 2,431,430 | 11/1947 | Shaw | 384/285 |
| 2,757,055 | 7/1956 | Davis | 384/293 |
| 3,058,791 | 10/1962 | Stallman | 384/293 |
| 3,909,087 | 9/1975 | Cairns | 384/293 |

FOREIGN PATENT DOCUMENTS

| | | | |
|---|---|---|---|
| 60-135564 | 7/1985 | Japan | C23C 14/06 |
| 276925 | 3/1990 | Japan | F16C 33/10 |

Primary Examiner—Lenard A. Footland
Attorney, Agent, or Firm—Sughrue, Mion, Zinn, Macpeak & Seas

[57]  ABSTRACT

In the slide member, a recessed and projected pattern is formed in a slide surface of a mother member of the slide member allowed to slide in contact with a mating member, recessed portions of the recessed and projected pattern are filled with a lubricant, and the area ratio of the recessed portions is set in a range of 30 to 70% while the depth thereof is set for 10 μm or less. The slide member is able to secure the lubricating property, wear resisting property and seize-up resisting property of the slide surface thereof with the recessed and projected pattern formed therein for a long period.

10 Claims, 4 Drawing Sheets

WEAR RESISTING SLIDE MEMBER

BACKGROUND OF THE INVENTION

The present invention relates to a slide member having a slide surface allowed to slide in contact with another member and treated for wear resistance and low friction resistance. In particular, the present invention relates to a slide surface structure of a wear resisting slide member useful for application to ordinary machine parts capable of relative sliding contact with each other, a slide bearing to be used in a vacuum, the inner and outer race surfaces of a ball-and-roller bearing, the thrust receive portion of a groove bearing, or the sliding contact portion of an artificial joint and the like.

As a pair of slide members arranged to slide in contact with each other and including a slide surface which is treated for wear resistance, for example, there are known metal slide members which are disclosed in Unexamined Japanese Patent Publication No. Sho. 60-135564. According to this publication, a wear resisting hard material and a solid lubricant are divided into blocks and are then evaporated spatteringly onto the slide surface of at least one of the two metal member arranged to slide in contact with each other to thereby provide an evaporated surface having a mottled pattern or a dimple pattern (which will be hereinafter referred to as a mottled pattern) formed by the hard material evaporated portions and solid lubricant material evaporated portions. According to this structure, loads are received by the hard material portions arranged to come into sliding contact with the mating metal member, and the solid lubricant disposed so as to surround the hard materials is dug up by sliding in contact with the mating metal member and is then supplied to the hard material portions as a lubricant, so that the wear resistance of the slide metal members can be increased and at the same time the friction thereof can be reduced.

In another conventional example, there is known a wear resisting slide member in which a projected and recessed surface is formed on the surface of the mother member of the slide member, a solid lubricant film is formed directly on the projected and recessed surface or a hard material layer is formed on the projected and recessed surface so far as the projected and recessed shape can be maintained and, after then, a solid lubricant film is formed in the recessed portions of the upper-most layer, which prevents the solid lubricant film from being peeled off due to shearing stresses produced during the sliding movement and also makes it possible to perform its wear resisting property and a sufficient lubricating property (see Unexamined Japanese Patent Publication No. Hei. 2-76925).

In both of the conventional metal slide member and wear resisting slide member, while the slide member is in sliding movement, the lubricant is supplied from the solid lubricating surface thereof to the wear resisting hard material surrounding the solid lubricating surface or to the projected portions of the sliding surface of the mother member thereof, so that there can be obtained a high lubricating property; and, since the loads are received by the wear resisting hard material or by the projected portions of the projected and recessed pattern, the load capacity as well as dimensional accuracy of the slide member can be improved. However, the above-mentioned Unexamined Japanese Patent Publication No. Sho. 60-135564 teaches only that an area ratio between the two materials of the mottled pattern of the slide surface of the slide member including the hard material portion and solid lubricant material portion is determined experimentally according to the using conditions of the respective members, and the area ratio is not specified concretely. Also, in the teachings of the Unexamined Japanese Patent Publication No. Hei. 2-76925, although the diameters of the respective tubular or cylindrical recessed or projected portions are shown, the number of them as well as the distribution of them are not shown, that is, the area ratio of the recessed or projected portions with respect to the whole slide surface are not illustrated.

In the slide member with the projected and recessed pattern formed in the above-mentioned manner, since a load is received by the projected portions and the lubricant is supplied from the recessed portions, if the area of the projected portions is small, then the load resisting property of the slide member is lowered and, on the other hand, if the area of the whole projected portions is great or the area of the recessed portions is small, then the capacity of supply of the lubricant is lowered. And, if the depth of the recessed portion is great, then the lubricant is difficult to flow out from the recessed portions and, if the recessed portion is too shallow in depth, then the lubricant cannot be held effectively. Therefore, in order to perform the low friction resistance and wear resistance of the slide member to the full, it is necessary to set the area ratio between the recessed and projected portions of the projected and recessed pattern and the depth of the recessed portion for the optimum values respectively.

SUMMARY OF THE INVENTION

In view of the above, it is an object of the present invention to provide a slide member which can secure the lubricating property, wear resistance and seize-up resistance of the slide surface thereof including a recessed and projected pattern by determining the area ratio between the recessed and projected portions and the depth of the recessed portions in an optimum range.

In attaining the above object, according to the present invention, there is provided a wear resisting slide member, in which a recessed and projected pattern is formed in the slide surface of the mother member of the slide member to slide in contact with another member, the recessed portions of the recessed and projected pattern are filled with a lubricant, the area ratio of the recessed portions with respect to the whole slide surface is set in the range of 30 to 70%, and the depth of the recessed portion is set to 1 mm or less, preferably, 10 μm or less.

According to an aspect of the present invention, there is provided an artificial hip joint structure in which, as the above-mentioned recessed and projected pattern, a projected pattern including cylindrical projections or a recessed pattern including cylindrical recessed portions is formed in one or both of the relative slide surfaces (an artificial bone head or cover socket) of an artificial hip joint, the diameter of the cylindrical projected portions or recessed portions is of the order of 0.5 mm, and the pitch thereof is of the order of 1.2 mm.

According to the present slide member including on the surface of the mother member of the slide member a recessed and projected surface having an area ratio of recessed portions of 30 to 70% and the depth of the recessed portion of 1 mm or less, or in order to reduce a working time, preferably, 10 μm or less, a lubricant is restricted by the recessed and projected portions serving as the foundation thereof, recessed portions play the role of a supplier of the lubricant, and a load is received by the projected portions, so that the lubricating property of the slide surface thereof can be maintained for a long period of time.

Also, by providing a hard material layer on the surface of the slide member so far as the shape of the recessed and projected surface can be maintained, even when the lubricant is left no longer, the hard material layer serves as a wear barrier, which can provide a higher wear resistance and a higher seize-up resistance.

Further, even if wear is caused in the slide part of the slide member, the present slide member allows the worn powder to escape into the recessed portions to thereby prevent the rapid wear of the slide part due to the worn powder.

DETAILED DESCRIPTION OF THE PREFERRED EMBODIMENTS

Figure 1:
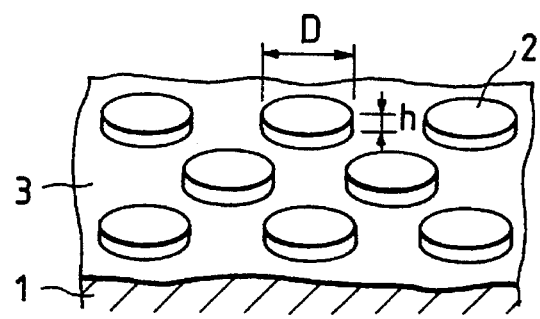
FIG. 1 is a partially perspective view of a first embodiment of a wear resisting slide member including a projected pattern according to the present invention.
Figure 2:
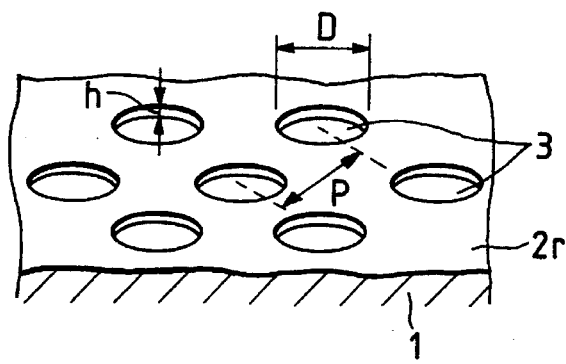
FIG. 2 is a partially perspective view of a second embodiment of a wear resisting slide member including a recessed pattern according to the present invention.

Description of the present invention will be given below by way of the embodiments thereof with reference to the accompanying drawings. FIGS. 1 and 2 are partially perspective views of slide surfaces of wear resisting slide members respectively disclosed as embodiments of the present invention. A mother member 1 can be formed of any of various industrial materials which includes metal such as iron, carbon steel, stainless steel and the like, non-ferrous metal such as copper, aluminum, platinum, titanium, titanium alloy and the like, resin materials such as ultra high molecular weight polyethylene, PPS (polyphenylene sulfide), polyamideimide-polyimide, polyimide, phenol, PES (polyethylene sulfide), PEEK (polyether etherketone) and the like, and a ceramic material such as aluminum oxide, diamond, sapphire, silicon nitride, silicon carbide, zirconia (zirconium oxide), silica (silicon oxide), titania (titanium oxide) and the like. A coating material for a coating film (a hard material film) which is alternatively formed on a slide surface of the mother member 1 is selected from titanium nitride, diamond, the above-described ceramic material, a nitride hardened metal surface and the like. A solid lubricant is selected from polyethylene, fluorocarbon polymer, nylon, polyacetal, polyolefin, polyester, metal soap, molybdenum sulfide, tungsten sulfide, boron nitride, graphite, calcium fluoride, barium fluoride and the like.

Figure 7:
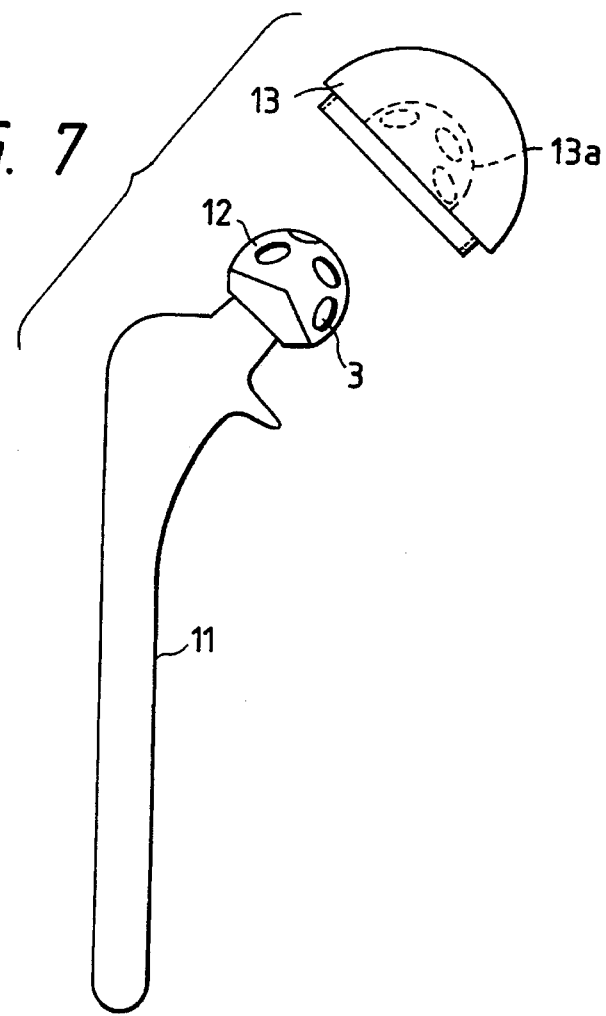
FIG. 7 is an exploded side view of an artificial hip joint to which the present invention is applied.

In an artificial joint which is an applicable example of the present invention as shown in FIG. 7 (a structure of the artificial joint will be described in more detail hereinafter), a material of a mother member (a ball 12 and a cover socket 13) is selected from cobalt-chrome alloy, zirconia, ultra high molecular weight polyethylene and the like. In the artificial joint, a coating material which is alternatively subjected to a surface of the mother member can be applied by evaporating titanium nitride to form projected portions. In the case where the mother member is formed of cobalt-chrome alloy, the surface of the mother member can be nitrided to harden the surface. Further, a lubricant of the artificial joint is selected from physiological saline, calf bovine serum, fat, fat oil, lard, blubber, suet, joint liquid and similar liquid thereof.

According to a first embodiment of the present invention shown in FIG. 1, in the slide surface of the mother member 1, a plurality of cylindrical projected portions 2 are provided regularly at equal distances, and the other portions of the slide surface than the projected portions 2 provide recessed portions 3, whereby the slide surface of the mother member 1 is formed in a recessed and projected pattern consisting of the projected portions 2 and recessed portions 3. When the diameter of each of the projected portions 2 is expressed as D and the number of the projected portions 2 is expressed as N, then the sliding contact area of the projected portions 2 with respect to the whole slide surface can be given by $\pi ND^2/4$, and the remaining areas of the slide surface other than the sliding contact area occupy a ratio of 30 to 70% with respect to the whole slide surface, which forms the recessed portions 3.

In a second embodiment shown in FIG. 2, a plurality of recessed portions 3 each having a diameter D are formed regularly at equal distances in the slide surface of the mother member 1, and the other portions of the slide surface than the recessed portions 3 provide projected portions 2 in the slide surface. In the second embodiment, the area ratio of the recessed portions is set in the range of 30 to 70% with respect to the whole slide surface. As shown in FIG. 2, when a diameter of the recessed portion 3 (similarly, a diameter of the projected portion 2 shown in FIG. 1) is converted into a circular diameter Deq, the following equation is obtained:

$$Deq_{(mm)} = \sqrt{\frac{4}{\pi} A}$$

where A (mm$^2$) is defined by an area per one of the recessed portions (or projected portions).

There will be described below a preferable structure of the recessed and projected pattern of the present invention, accompanying the reason in the second embodiment as shown in FIG. 2. Since the opposite reason can be applied to the first embodiment, the description is omitted.

The circular diameter of the recessed portion 3 is preferable within a range of 0.2 to 0.8 mm. When the circular diameter of the recessed portion 3 is less than 0.2 mm, it is equivalent to that the projected and recessed pattern vanishes practically, so that the necessary amount of the lubricant is not stored in the recessed portions 3. Further, the worn lubricant and worn powder on the projected portions 2 cannot be stored in the recessed portions 3. When the circular diameter of the recessed portion 3 is more than 0.8 mm, the area of the projected portions 2 decreases practically so that the projected portions 2 cannot support the loads, whereby the sliding and lubricating properties are deteriorated due to wear of the slide surface and occurrence of minute unevenness.

Further, in the second embodiment, when a pitch P between the recessed portions 3 is defined by a distance from a geometrical center of the recessed portion 3 to that of the adjacent recessed portion 3, the pitch P is preferable within a range of 0.8 to 1.6 mm. When the pitch P is less than 0.8 mm, the area for supporting the loads is insufficient so that the area of the projected portions 2 is small, whereby the slide surface is rapidly worn. When the pitch P is more than 1.6 mm, it is difficult that the lubricant in the recessed portions 3 is transferred to the projected portions 2. Further, the recessed portions 3 is difficult to store the lubricant and worn powder on the projected portions 2.

The projected and recessed pattern is formed in a depth of 1–10 μm on the surface of the mother member 1 by means of etching, spattering, beam processing (electron laser) or the like. The coating film is alternatively formed by either of spatter, ion plating, evaporation, wet plating and the like. The coating film can be employed to form the projected portions 2 of the slide surface. Then, the solid lubricant is applied to the projected and recessed pattern to form a solid lubricant film of 1–10 μm in thickness by the same means as to form the coating film. Though the mother member 1, the coating film and the solid lubricant film are formed in order, the projected and recessed pattern of 1–10 μm in depth formed on the surface of the mother member 1 is subjected to the recessed portions 3 which is similarly formed in a depth of 1–10 μm on the solid lubricant film. Even if the solid lubricant on the projected portions is worn by loads, the worn solid lubricant is transferred to the recessed portions, so that the solid lubricant on the recessed portions can be transferred to the projected portions again by a required amount. Such a structure can improve effects of the wear resistance, lower torque, lower friction and the like. Particularly, for use in the artificial joint, there is none of space where the worn powder is escaped. Therefore, the recessed portions can serve as a kind of storage for the excess lubricant and worn powder, and as a source for supplying the lubricant to the slide surface, so that the further effects can be attained.

The recessed and projected pattern is not always limited to the above-mentioned cylindrical or tubular shape, but other shapes can be employed; for example, the recessed and projected portions may be formed in a rectangular or other polygonal shape, or the recessed portions and projected portions may be arranged such that they are divided into layers. In any case, the recessed and projected portions must be arranged regularly over the whole slide surface, and the area ratio of the recessed portions must be in the range of 30 to 70% with respect to the whole slide surface.

Figure 3:
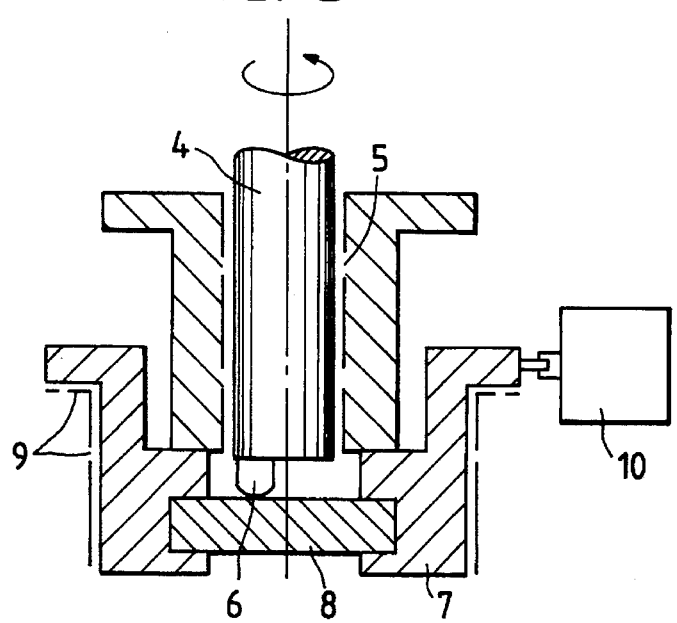
FIG. 3 is a schematic longitudinal section view of a wear and friction test device employed in the present invention.
Figure 4:
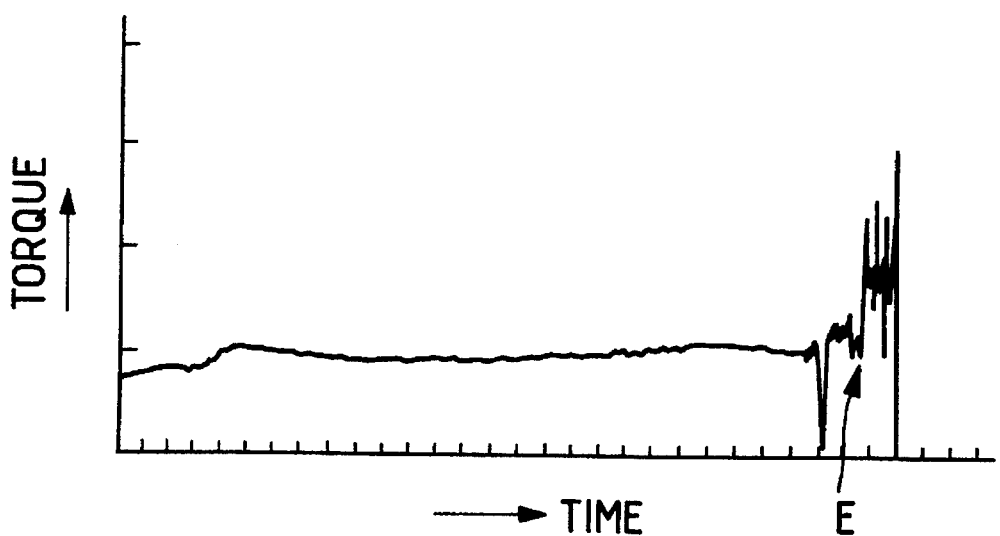
FIG. 4 is a graphical representation of a time-torque characteristic obtained in a wear and friction test.

The reason why the area ratio of the projected portions 2 or recessed portions 3 is set in the range of 30 to 70% will be described below by means of a concrete wear and friction test. At first, there is shown in FIG. 3 a friction and wear test device which is employed in the present invention. In the test device, there is provided a rotary shaft 4 which is supported vertically by an air bearing 5, a sphere-shaped contact member 6 is fixed to the lower end of the rotary shaft 4 eccentrically from the axis of the rotary shaft 4, and a specimen 8 mounted to a specimen mount base 7 is in contact with the contact member 6. The rotary shaft 4 and specimen mount base 7 are arranged such that loads are being applied to them in the axial direction thereof and, therefore, the pressure contact forces of the contact member 6 and specimen 8 can be adjusted. The specimen mount base 7 is supported by an air bearing 9 in a thrust direction as well as in a radial direction. The outside portion of the specimen mount base 7 is connected to a load cell 10 which is fixedly installed. By driving rotationally the rotary shaft 4 round the axis thereof by a variable speed motor (which is not shown), the load of the specimen mount base 7 in the rotational direction thereof due to a friction force produced between the contact member 6 and specimen 8 can be detected by the load cell 10, and the change with the passage of time of the friction force between the contact member 6 and specimen 8 can be observed. The time-torque characteristic obtained according to this method is generally expressed as shown in FIG. 4, and the life of the specimen is determined by the time when the torque change starts to increase suddenly and heavily (E point).

As described above, in the slide member with the recessed and projected pattern, the load is received by the projected portions and the lubricant is supplied from the recessed portions. If the area ratio of the projected portions is decreased, then the load resisting capacity of the slide member is lowered and, if the area ratio of the recessed portions is decreased, then the capacity of the slide member to supply the lubricant is lowered. This shows that, in a slide surface, there exists the optimum area ratio between the projected and recessed portions. Also, if the depth of the recessed portion is too great, then the lubricant is difficult to flow out to the slide surface and, if it is too shallow, then the supply of the lubricant runs short. Therefore, as to the depth h of the recessed portions as well, there is present the optimum value. In connection with the slide surface including a projected pattern consisting of the cylindrical projected portions 2 as shown in FIG. 1, the present inventors produced a specimen by changing the area ratio of the whole recessed portions 3 relative to the whole slide surface and also by coating molybdenum sulfide spattered films ($MoS_2$) onto the recessed portions as the solid lubricant films; and, the life of the coated films of the specimen was tested. The resultant test data are shown in Table 1. In this test, the depths of the recessed portions were respectively set as 10 μm.

TABLE 1

| Types of Patterns | Projected Type | | | | | None |
|---|---|---|---|---|---|---|
| Area Ratios of Recessed Portions | 14% | 30% | 50% | 70% | 80% | — |
| Life (H) | 2 | 17 | 39 | 28 | 2 | 1 |

In this test, the number of revolutions of the rotary shaft 4 was set for 1000 rpm, the pressing load of the contact member was set for 0.23 kgf, and the sliding speed was set for 0.4 m/s. When the area ratio of the recessed portions 3 was 14%, lubrication was short and, after 2 hours, the torque was increased suddenly; and, if the area ratio exceeded 80%, then the projected portions 2 collapsed so that they were not be able to receive the loads. In Table 1, "None" for the types of patterns means that the slide surface foes not include any projected or recessed portions.

In a second test, a projected and recessed pattern including such cylindrical recessed portions 3 as shown in FIG. 2 was formed in the slide surface of the slide member, the area ratio of the recessed portions 3 was changed to other various ratios, and the $MoS_2$ spattered film was coated on the slide surface as the solid lubricant film. The resultant test data of the lives of the film are shown respectively in Table 2. In the second test, the depths of the recessed portions 3 were respectively set or 10 μm. In this test as well, when the area ratio of the recessed portions was 14%, then lubrication runs short and, when the area ratio was 80%, then the load capacity of the slide member was lowered. In the case of a specimen in which no recessed and projected pattern was formed and the $MoS_2$ film was spattered only (which is shown in Table 2 as "None"), the load capacity thereof was small and the life of the film was 1 hour.

TABLE 2

| Types of Patterns | Recessed Type | | | | | None |
|---|---|---|---|---|---|---|
| Area Ratios of Recessed Portions | 14% | 30% | 50% | 70% | 80% | — |
| Life (H) | 3 | 17 | 36 | 25 | 2 | 1 |

The life of the coated film was also connected with the depths of the recessed portions of the recessed and projected patterns. In a wear test using the device shown in FIG. 3, when the wear conditions of the slide surface is observed by a roughness gauge, for a slide surface with ultra high molecular weight polyethylene coated on the surface thereof, the wear difference thereof is found great according to whether a projected and recessed pattern is formed on the slide surface or not. When the slide surface with no projected and recessed pattern applied was observed by the roughness gauge, then great damages were found. This seems that the slide surface was shaved deeply by the worn powder. That is, the worn powder itself causes new wear. On the other hand, in the case of the slide surface with a projected and recessed pattern formed therein, in addition to the supply of the lubricant from the recessed portions, the eared powder is allowed to escape into the recessed portions, which prevents the eared powder from entering the projected portions of the slide surface.

Now, in Table 3, there are shown the test data on the film lives obtained from a third test in which, in connection with a slide surface formed with such a recessed and projected pattern as shown in FIG. 2, the area ratio of the recessed portions 3 with respect to the whole slide surface was set for 70%, the groove depth h of the recessed portions 3 was changed, and $MoS_2$ spattered films were coated on the slide surface as the solid lubricant film.

TABLE 3

| Types of Patterns | Recessed Type | | | | | None |
|---|---|---|---|---|---|---|
| Groove Depths h (μm) | 1 | 5 | 7 | 10 | 15 | — |
| Life (H) | 50 | 120 | 32 | 25 | 1 | 1 |

Those data show that, if the groove depth exceeds 15 μm, then the lubricant is collected into the bottoms of the recessed portions 3, which prevents the lubricant from flowing up to the projected portions 2 and thus the life of the coated film is shortened greatly.

In the slide surface structure according to the present invention, the area ratio of the recessed portions of the projected and recessed pattern is set in the range of 30 to 70% and the groove depths of the recessed portions are set in the range of 1 μm to 10 μm. It can be understood from the above-mentioned test results as well that the slide surface including the projected and recessed pattern of the above ranges is able to perform the low friction resisting property and wear resisting property thereof to the greatest degree.

Figure 5:
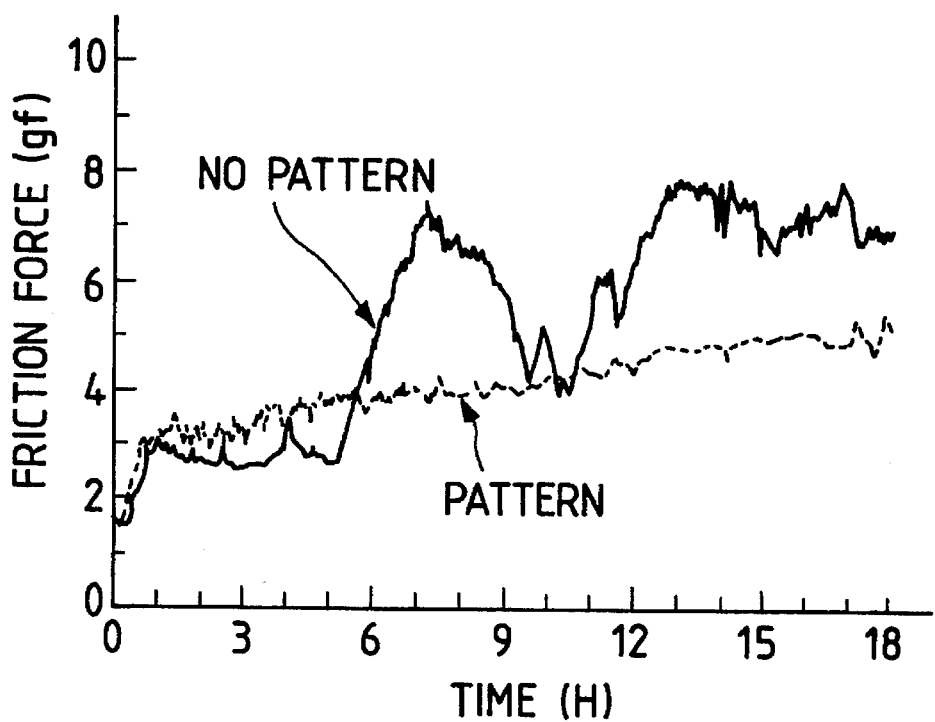
FIG. 5 is a graphical representation of variations in a friction force with the passage of time obtained in a friction test conducted on a combination of ultra high molecular weight polyethylene and a titanium nitride (TiN) coating material.

The present invention can be practically applied in various ways, e.g., for use of an artificial joint. In more detail, the surface property of the relative slide parts of the artificial joint can be improved by the present invention. In the artificial joint, an artificial bone head and a cover socket fittable with each other are generally formed of metal or a combination of ceramics and ultra high molecular weight polyethylene. The inventors conducted a test by using the wear and friction test device shown in FIG. 3. That is, in this test, a contact member was formed of ultra high molecular polyethylene finished to a plane shape and a specimen was formed of a stainless steel member and titanium nitride (TiN) highly adaptable to a living body coated on the stainless steel member. In FIG. 5, there are shown variations in the friction force which were obtained in this test. This figure shows that, when a specimen including no pattern was used, the variations in the friction force were great and unstable. On the other hand, when a specimen including a recessed and projected pattern was used, the variations in the friction force was small and stable. On the surface of the TiN of the specimen, it is difficult from the observation after the test to find a difference between the worn conditions respectively produced when the projected and recessed pattern was formed or not. On the other hand, as to the ultra high molecular weight polyethylene as the solid lubricant, the observation shows that the specimen with no projected and recessed pattern wears much more when compared with the specimen including a projected and recessed pattern. Also, the roughness of the specimen with no projected and recessed pattern was measured, there were found great damages. It can be imagined that the damages were caused when the specimen was deeply shaved by the wear pieces. On the other hand, when the pattern was added, the wear pieces are taken into the recessed portions and thus they do not come up onto the slide surface, which prevents heavy wear of the slide surface.

Figure 6:
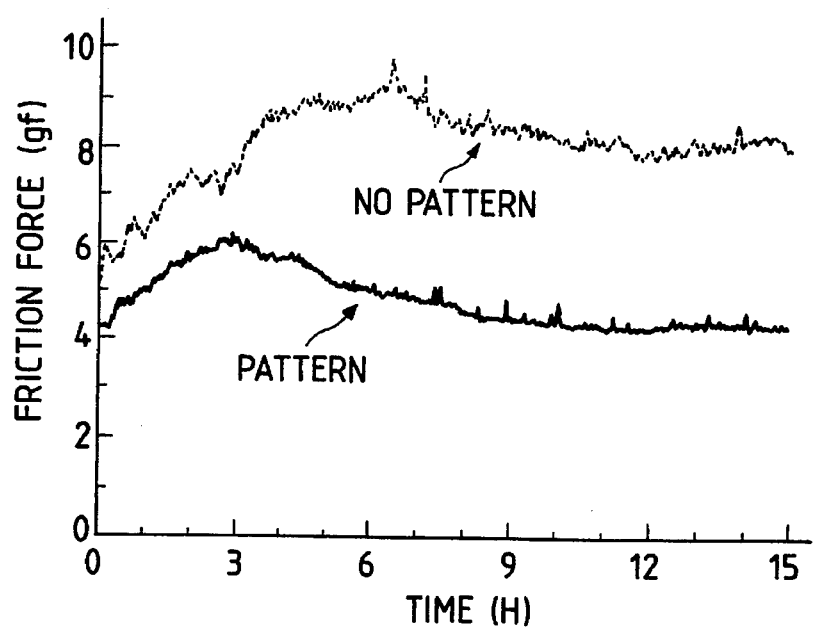
FIG. 6 is a graphical representation of variations in a friction force with the passage of time obtained in a friction test conducted in a physiological saline solution on a combination of ultra high molecular weight polyethylene and a titanium nitride (TiN) coating material.

Also, similarly, the inventors produced a specimen which includes a projected and recessed pattern in the slide surface thereof, coated TiN having an excellent adaptability to a living body on the slide surface of the specimen, used ultra high molecular weight polyethylene as a partner material, and conducted a friction test in a physiological saline solution. The variations in the frictional force with the passage of time obtained in the friction test are shown in FIG. 6. In FIG. 6, for comparison, there are also shown the variations in the friction force with the passage of the time obtained when a specimen with no projected and recessed pattern was tested under the same conditions. It can be seen clearly from FIG. 6 as well that the slide surface including the projected and recessed pattern is far advantageous.

In FIG. 7, there is shown an exploded side view of an artificial hip joint using a wear resisting slide surface structure according to the invention. In this artificial hip joint, a ball (an artificial bone head) 12 is mounted on the leading end of a stem 11, and a recessed spherical surface 13a of a cover socket 13, which is the mating member of the ball 12, can be fitted with the ball 12 in such a manner that they are slidable with respect to each other. In one or both of the respective slide surfaces of the ball 12 and socket 13, such a projected and recessed pattern including cylindrical projected portions 2 and cylindrical recessed portions 3 is formed as shown in FIG. 1 or FIG. 2. As the area ratio and depth of the recessed portions 3 of the projected and recessed portions, the values included in the above-mentioned ranges may be employed. Also, as the diameter and pitch of the individual projected portions 2 and recessed portions 3, there exist the optimum values when the invention is used as an artificial hip joint.

Figure 8:
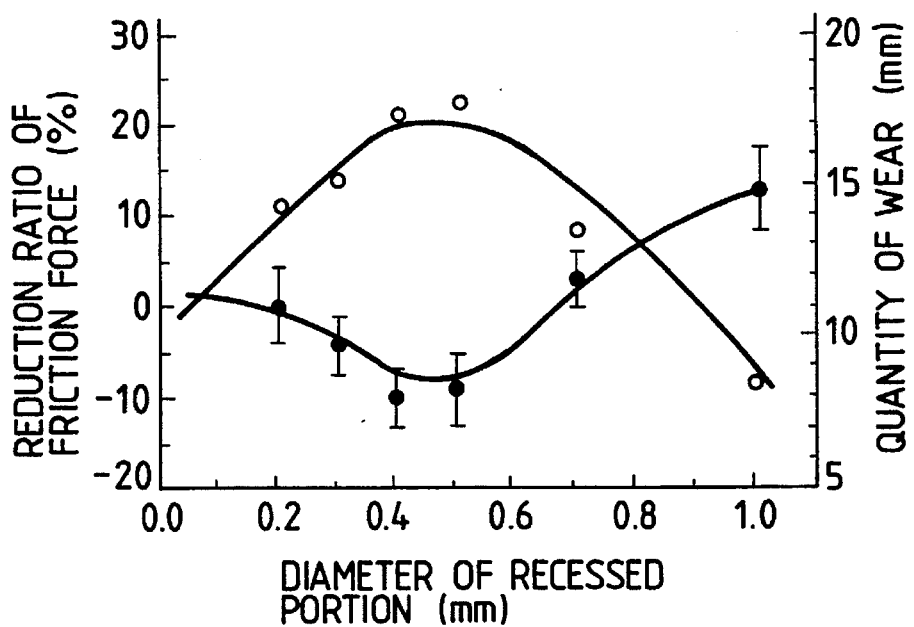
FIG. 8 is a graphical representation of the slide surface characteristic of an artificial hip joint with respect to the diameter of the recessed portions of a recessed and projected pattern formed in the slide surface according to the present invention.
Figure 9:
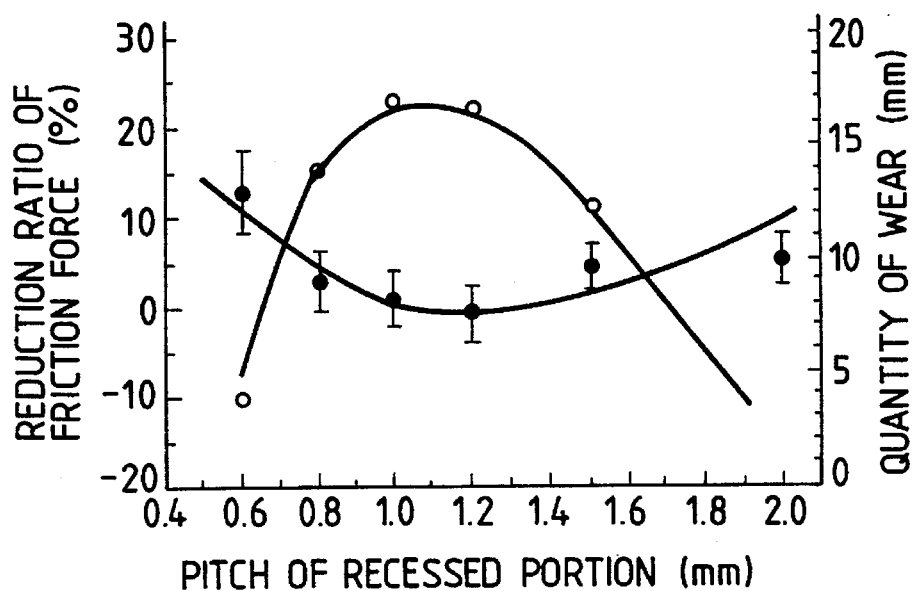
FIG. 9 is a graphical representation of the slide surface characteristic of an artificial hip joint with respect to the pitch of the recessed portions of a recessed and projected pattern formed in the slide surface according to the present invention.

In FIG. 8, there are shown the test results of the slide surface characteristic of an artificial hip joint with respect to the diameters (mm) of the cylindrical recessed portions of the projected and recessed pattern. Ultra high molecular weight polyethylene was used on the slide surface. In FIG. 8, white circles respectively show the values of a reduction rate (%) of a friction force with respect to the diameters of the recessed portions, while black circles respectively stand for the quantity (mm) of wear of the ultra high molecular weight polyethylene. In FIG. 9, similarly, there are shown the test results on the reduction rate (while circles) of the friction force and the quantity of wear (black circles) with respect to the pitches (mm) of the cylindrical recessed portions. As can be seen from the two figures, when the diameter D of the recessed portion is 0.5 mm and the pitch p (FIG. 2) is 1.2 mm, the reduction rate of the friction force is greatest and the quantity of wear of the ultra high molecular weight polyethylene is smallest. Therefore, in the artificial hip joint with a projected and recessed pattern, when the pattern diameter is 0.5 mm and the pitch is 1.2 mm, the lubricating property can be enhanced most. As in the prior art, as means for preventing the friction and wear of an artificial joint, a sufficient effect cannot be obtained only by the improvement of the material of the artificial joint. On the other hand, with use of the slide surface structure according to the invention, the lubricating property of the artificial joint slide surface can be improved and the life of the artificial joint can be extended to a great extent.

In the above description, the depth of the recessed portions is set for 1.0 mm or less, preferably, 10 μm. However, the depth may be selected according to cases in the above-mentioned range. For example, for a slide surface for use in an artificial hip joint, when the worn powder must be escaped into the recessed portions, the depth may be preferably set deeper and, when the recessed portions are filled with the solid lubricant, the depth may be preferably set shallower. On the other hand, from the viewpoint of machining, especially when the projected and recessed pattern must be formed according to a fine machining technique, the depth may be set shallower, preferably, the depth may be set for 10 μm or less.

As has been described heretofore, according to the present invention, the recessed and projected pattern is formed in the surface of the mother member to be in sliding contact with its mating member, and the area ratio of the recessed portions is set in the range of 30 to 70%, the depth of the recessed portions is set for 1.0 mm or less, or in order to reduce the time for machining the recessed and projected pattern, preferably, the depth is set for 10 μm or less. Owing to such a structure, under the solid lubricant conditions or in a liquid solution such as a physiological saline solution or the like, the lubricant can be supplied from the recessed portions and the worn powder is allowed to escape into the recessed portions to thereby prevent the abrasive wear, so that the wear resisting property and print resisting property of the slide member can be improved. Also, by providing a hard film formed of titanium nitride (TiN), titanium carbon (TiC), titanium boron (TiB$_2$) or the like, or by providing a hard layer formed of injected ions, even if the lubricant is left no longer, the hard film or layer prevents the slide surface from being worn, so that the slide surface according to the invention can be improved in the wear resisting property, seize-up resisting property and load capacity thereof. When the invention is applied to an artificial joint, then the characteristic of the slide surface of the artificial joint can be improved and, in particular, the friction and wear of the slide surface can be reduced to a great extent, so that the life of the artificial joint can be extended quite effectively.

What is claimed is:

1. A wear resisting slide member contacting with a mating member, comprising:

a mother member including a recessed and projected pattern formed in a slide surface contacting with said mating member, said recessed and projected pattern including a recessed portion and filled with a lubricant selected from a solid lubricant, a liquid lubricant and combination thereof, wherein said recessed portion holds an area within a range of 30 to 70% with respect to the whole of said slide surface, and includes the depth of 10 μm or less.

2. The wear resisting slide member of claim 1, wherein a diameter of said recessed portion formed substantially in a circular shape is 0.2 to 0.8 mm in a circular diameter.

3. The wear resisting slide member of claims 1 and 2, wherein a distance from a center of said recessed portion to that of an adjacent recessed portion is 0.8 to 1.6 mm.

4. A wear resisting slide member contacting with a mating member, comprising:

a mother member including a recessed and projected pattern formed in a slide surface contacting with said mating member, said recessed and projected pattern including a projected portion and filled with a lubricant selected from a solid lubricant, a liquid lubricant and combination thereof, wherein said projected portion holds an area within a range of 30 to 70% with respect to the whole of said slide surface, and includes the depth of 10 μm or less.

5. The wear resisting slide member of claim 4, wherein a diameter of said projected portion formed substantially in a circular shape is 0.2 to 0.8 mm in a circular diameter.

6. The wear resisting slide member of claims 4 and 5, wherein a distance from a center of said projected portion to that of an adjacent projected portion is 0.8 to 1.6 mm.

7. The wear resisting slide member of claims 1 to 6, wherein said slide surface is selected from a race surface of a ball-and-roller bearing, a thrust receive surface of a groove bearing and a sliding contact surface of an artificial joint.

8. The wear resisting slide member of claims 1 to 6, wherein said mother member is formed with at least one of:

metal selected from iron, carbon steel, stainless steel, cobalt-chrome alloy, copper, aluminum, platinum, titanium, titanium alloy, and non-ferrous metal;

a resin material selected from ultra high molecular weight polyethylene, polyphenylene sulfide, polyamideimide, polyimide, phenol, polyethylene sulfide, polyether etherketone and compound thereof; and a ceramic material selected from aluminum oxide, diamond, sapphire, silicon nitride, silicon carbide, zirconia, silica, titania and alloy thereof.

9. The wear resisting slide member of claims 1 to 6, wherein said slide surface of said mother member is coated with a coating material selected from titanium nitride, diamond, a ceramic material and alloy thereof, said solid lubricant is selected from polyethylene, fluorocarbon polymer, nylon, polyacetal, polyolefin, polyester, metal soap, molybdenum sulfide, tungsten sulfide, boron nitride, graphite, calcium fluoride, barium fluoride and compound thereof, and said liquid lubricant is selected from physiological saline, calf bovine serum, joint liquid and mixture thereof.

10. The wear resisting slide member of claims 1 to 6, wherein the wear resisting slide member comprises an artificial joint composed of a ball and a socket serving as said mother member, each of said ball and socket is formed of a material selected from cobalt-chrome alloy, zirconia, ultra high molecular weight polyethylene, a coating material for coating slide surfaces of said ball and socket is selected from titanium nitride, nitride hardened metal surface, and said lubricant is selected from physiological saline, calf bovine serum, fat, fat oil, lard, blubber, suet, joint liquid and mixture thereof.

* * * * *